US010478064B2

(12) United States Patent
Walmsley et al.

(10) Patent No.: US 10,478,064 B2
(45) Date of Patent: Nov. 19, 2019

(54) DEVICE FOR DETERMINING AN INTRAOCULAR PRESSURE OF AN EYE

(71) Applicant: INGENEUS PTY LTD, Mt. Waverley, Victoria (AU)

(72) Inventors: Richard Gordon Walmsley, Balwyn North (AU); David James Lockwood, Balwyn North (AU); Michael Andrew Coote, Balwyn North (AU)

(73) Assignee: INGENEUS PTY LTD., Mt. Waverley Victoria (AU)

(*) Notice: Subject to any disclaimer, the term of this patent is extended or adjusted under 35 U.S.C. 154(b) by 476 days.

(21) Appl. No.: 15/037,974

(22) PCT Filed: Nov. 19, 2014

(86) PCT No.: PCT/AU2014/001051
§ 371 (c)(1),
(2) Date: May 19, 2016

(87) PCT Pub. No.: WO2015/074094
PCT Pub. Date: May 28, 2015

(65) Prior Publication Data
US 2016/0296113 A1    Oct. 13, 2016

(30) Foreign Application Priority Data
Nov. 19, 2013 (AU) ................ 2013904472

(51) Int. Cl.
*A61B 5/00* (2006.01)
*A61B 3/16* (2006.01)
*A61B 17/00* (2006.01)

(52) U.S. Cl.
CPC ...... *A61B 3/16* (2013.01); *A61B 2017/00907* (2013.01); *A61B 2560/0223* (2013.01); *A61B 2560/0418* (2013.01); *A61B 2562/12* (2013.01)

(58) Field of Classification Search
CPC ............... A61B 3/16; A61B 2562/12; A61B 2560/0223; A61B 2560/0418; A61B 2017/00907
See application file for complete search history.

(56) References Cited

U.S. PATENT DOCUMENTS 1,419,134 A    6/1922  Goldstein
2,314,514 A *  3/1943  Parsons .................... A61B 3/16
                                                    600/398
(Continued)

FOREIGN PATENT DOCUMENTS

AT    168085 B  *  4/1951
DE    3018084 A1    11/1981
(Continued)

OTHER PUBLICATIONS

Preliminary Rejection for Korean Patent Application No. 10-2017-7000350.
(Continued)

*Primary Examiner* — Max F Hindenburg
(74) *Attorney, Agent, or Firm* — Tarolli, Sundheim, Covell & Tummino LLP

(57) ABSTRACT

A device for determining an intraocular pressure of an eye is disclosed. The device comprises; (a) a housing; (b) a plunger axially movable within the housing, a first end of the plunger having a tip for contacting the eye; (c) an indicator arm operatively connected to a second end of the plunger; (d) a measurement gauge for indicating the intraocular pressure of the eye; and (e) a resilient biasing member for biasing the plunger towards an extended position in which the plunger tip protrudes beyond the housing and the indicator arm is biased towards a first position on the measurement gauge. Applying pressure to the eye via the plunger tip causes the intraocular pressure of the eye to exert an opposing force on the plunger tip causing the plunger to
(Continued)

retract into the housing to cause a reciprocal movement of the indicator arm towards a second position thereby indicating the intraocular pressure of the eye on the measurement gauge.

20 Claims, 4 Drawing Sheets

(56) References Cited

U.S. PATENT DOCUMENTS

| | | | |
|---|---|---|---|
| 2,656,715 A | | 10/1953 | Tolman |
| 2,882,891 A | | 4/1959 | Husted |
| 3,150,520 A | | 9/1964 | Mackay et al. |
| 3,359,789 A | | 12/1967 | Forse |
| 3,952,585 A | * | 4/1976 | Perkins ............. A61B 3/16 600/405 |
| 5,735,275 A | | 4/1998 | Ballou et al. |
| 6,251,071 B1 | * | 6/2001 | Fresco ............. A61B 3/16 128/898 |

FOREIGN PATENT DOCUMENTS

| | | | | |
|---|---|---|---|---|
| DE | 3018084 C2 | * | 4/1983 | ......... A61B 3/16 |
| FR | 1419130 A | | 10/1965 | |
| GB | 191105356 A | | 2/1912 | |
| SU | 1666060 A1 | | 7/1991 | |
| WO | 1997043946 A | | 11/1997 | |
| WO | 2007/071446 A1 | | 6/2007 | |

OTHER PUBLICATIONS

Supplementary European Search Report for Application No. 14864970. 0-1666/3071091, dated Jul. 26, 2017.

* cited by examiner

DEVICE FOR DETERMINING AN INTRAOCULAR PRESSURE OF AN EYE

FIELD OF THE INVENTION

The present invention relates generally to devices and methods for determining the intraocular pressure of a patient's eye. Such devices are generally referred to as tonometers. In a particular form, the present invention relates to devices and methods for determining the intraocular pressure of the eye in which the gauge and device indicator arm are comprised within the device housing.

BACKGROUND TO THE INVENTION

The correlation between increased intraocular pressure (IOP) and loss of sight due to glaucoma diseases has been acknowledged for some time. As a result, determining intraocular pressure is integral to ophthalmic examinations.

Various methods and corresponding devices, or tonometers, for determining intraocular pressure are known. These include invasive methods, wherein pressure sensors are inserted directly into the eye, and non-invasive methods which may involve a measurement apparatus which contacts the eye directly during measurement, or contactless measurement apparatus such as air-puff type tonometers which measure corneal deformation in response to a stream of air blown onto the surface to the eye.

In applanation tonometry the intraocular pressure is inferred from the force required to applanate or flatten a constant area of the cornea. The Maklakoff tonometer was an early example of an applanation tonometer, while the Goldmann tonometer is the most widely used version in current practice. An advantage of Goldmann applanation tonometry is that the tonometer is mounted on a slit lamp microscope, providing a stable base from which to handle the instrument and take measurements. However, the slit lamp mount is also disadvantageous since it means that the Goldmann tonometer is inherently not portable. Another disadvantage is that fluorescein dye and a topical anaesthetic must be introduced onto the surface of the eye. The fluorescein dye aids in viewing the mires and the anaesthetic is required since the tip of the device touches the cornea.

Indentation tonometry measures the depth of corneal indentation caused by a small plunger carrying a known weight. The indentation of the corneal surface is indirectly proportional to the intraocular pressure. For very high levels of intraocular pressure, extra weights can be added to cause the plunger to apply additional pressure to the cornea. The extent of movement of the plunger is measured using a calibrated scale.

The Schiøtz tonometer is the most common device and is based on the indentation tonometry principle. The Schiøtz tonometer consists of a curved footplate, which is placed on the cornea of a supine patient. A weighted plunger attached to the footplate sinks into the cornea. A scale provides a reading depending on how much the plunger sinks into the cornea, and a conversion table converts the scale reading into intraocular pressure measured in mmHg.

A limitation of the Schiøtz tonometer is that it must be used on a supine patient, so that the device is in the vertical position during use. Moreover, the weights must be adjusted for different intraocular pressure ranges. The Schiøtz tonometer can be difficult to use, particularly for operators with limited training.

Objects and advantages of the invention will become apparent to those of ordinary skill in the art having reference to the following specification together with its drawings.

SUMMARY OF THE INVENTION

The present invention is directed to devices and methods for determining the intraocular pressure of a patient's eye.

In a broad form, the present invention relates to devices and methods for determining the intraocular pressure of the eye in which the gauge and device indicator arm are comprised within the device housing.

According to a first aspect of the present invention, there is provided a device for determining an intraocular pressure of an eye comprising:
(a) a housing;
(b) a plunger axially movable within the housing, a first end of the plunger having a tip for contacting the eye;
(c) an indicator arm operatively connected to a second end of the plunger;
(d) a measurement gauge for indicating the intraocular pressure of the eye;
(e) a resilient biasing member for biasing the plunger towards an extended position in which the plunger tip protrudes beyond the housing and the indicator arm is biased towards a first position on the measurement gauge; wherein applying pressure to the eye via the plunger tip causes the intraocular pressure of the eye to exert an opposing force on the plunger tip causing the plunger to retract into the housing to cause a reciprocal movement of the indicator arm towards a second position thereby indicating the intraocular pressure of the eye on the measurement gauge.

The gauge and device indicator arm may be comprised within the housing.

The indicator arm may pivot in a plane parallel to the longitudinal axis of housing.

The measurement gauge may be adjusted within the housing during assembly for pressure reading calibration.

The indicator arm may be counterbalanced about a pivot point, with a counterbalance, such that the device can be used to determine the intraocular pressure of the eye at any angle. That is, the device may be used on a patient who is sitting, or supine, for example.

The indicator arm, resilient biasing member, and counterbalance may be integrated into a single piece.

In embodiments wherein the transparent window is located at the proximal end, the counterbalance may be positioned at the distal end and the indicator arm may point towards the eye. In embodiments wherein the transparent window is located at the distal end, the counterbalance may be positioned at the proximal end and the indicator arm may point away from the eye.

The housing may comprise a transparent window to allow viewing of the measurement gauge. The transparent window may be located at a proximal end of the device, near where contact is made with the eye, or at a distal end of the device, away from where contact is made with the eye.

The first position on the measurement gauge may correspond to a null reading. That is, the indicator arm could indicate a null reading when the device is not in use, or in use if the intraocular pressure of the eye was zero mmHg. Alternately, the resting position may correspond to a predetermined intraocular pressure, for example 10 mmHg.

In an embodiment, the housing comprises a tube-like portion at one end through which the plunger tip protrudes in the extended position. The tube-like shape of this portion may serve as a guide for axial movement of the plunger within the housing.

Preferably, the tube-like portion further comprises a footplate having an aperture through which the plunger tip protrudes. The footplate may comprise a concave surface that runs substantially perpendicular to a longitudinal axis of the tube-like portion. The concavity of the surface is intended to correspond to the shape of the cornea of a human eye.

In one embodiment, the footplate is transparent to allow the operator to easily identify when the footplate makes contact with a cornea of the eye.

A high intraocular pressure causes a greater retraction of the plunger into the housing thereby resulting in a greater reciprocal movement in the indicator arm to indicate a high intraocular pressure reading on the measurement gauge.

Conversely, a low intraocular pressure causes a lesser retraction of the plunger into the housing thereby resulting in a lesser reciprocal movement in the indicator arm to indicate a low intraocular pressure reading on the measurement gauge.

An intraocular pressure approaching a maximum intraocular pressure may cause the plunger tip to retract into the housing to the extent that the plunger tip lies substantially flush with the concave surface of the footplate of the tube-like portion.

A diameter of the plunger tip may correspond substantially to the diameter of an iris of the eye. The plunger tip may have a concave contact surface. The concavity of the surface is intended to correspond to the shape of the cornea of a human eye. Alternately, the plunger tip may have a plane contact surface.

In an embodiment, the resilient biasing member includes an elastomeric spring element.

A first end of the resilient biasing member may be coupled to the indicator arm. A second end of the resilient biasing member may be fixed in position within the housing. Alternately, the position of the second end of the resilient biasing member may be adjustable relative to the housing. Adjustment of the position of the second end of the resilient biasing member relative to the housing allows calibration of the force applied by the resilient biasing member to the indicator arm.

In one embodiment, the position of the second end of the resilient biasing member may be adjustable along a linear rack. The linear rack may include a plurality of teeth to facilitate adjustment of the position of the resilient biasing member.

In another embodiment, the length of the resilient biasing member may be adjustable. The length may be adjustable with a screw knob which may be adjusted to lengthen or shorten the resilient biasing member.

In one form of the present invention, the measurement gauge provides a reading of the intraocular pressure in mmHg. That is, the measurement gauge may be calibrated so as to provide a direct reading of the intraocular pressure in mmHg. In another form of the present invention, the measurement gauge provides an indication of a LOW, MEDIUM or HIGH intraocular pressure. The measurement gauge may provide this indication using alphanumeric characters, colour coding, grayscale shading or other suitable means. The measurement gauge may be rotatable inside the housing to thereby calibrate the device. The calibration may be performed during assembly.

In one particular embodiment of the invention, the device is intended for single use.

According to another embodiment of the invention, the device is intended for single handed operation. The device may be used with either a left hand or a right hand.

In yet another embodiment, the device comprises a protective cap removably covering the plunger tip.

In one embodiment, the housing is encased in a sleeve, wherein the housing is axially moveable within the sleeve in a direction that is parallel to the longitudinal axis of the housing. The extent of movement of the housing within the sleeve may be calibrated to indicate to an operator of the device, when the operator should cease increasing the pressure applied to the eye. This level of pressure may correspond to the point where the operator should take a reading from the measurement gauge.

According to a second aspect of the present invention, there is provided a method for determining an intraocular pressure of an eye including the step of applying pressure to the eye of a patient using a device, the device comprising:
(a) a housing;
(b) a plunger axially movable within the housing, a first end of the plunger having a tip for contacting the eye;
(c) an indicator arm operatively connected to a second end of the plunger;
(d) a measurement gauge for indicating the intraocular pressure of the eye;
(e) a resilient biasing member for biasing the plunger towards an extended position in which the plunger tip protrudes beyond the housing and the indicator arm is biased towards a first position on the measurement gauge;
wherein applying pressure to the eye via the plunger tip causes the intraocular pressure of the eye to exert an opposing force on the plunger tip causing the plunger to retract into the housing to cause a reciprocal movement of the indicator arm towards a second position thereby indicating the intraocular pressure of the eye on the measurement gauge.

According to a third aspect of the present invention, there is provided a method for manufacturing a device for determining an intraocular pressure of an eye comprising:
assembling within a housing an axially moveable plunger, a first end of the plunger comprising a tip for contacting the eye, an indicator arm operatively connected to a second end of the plunger, a measurement gauge for indicating the intraocular pressure of the eye, and a resilient biasing member for biasing the plunger towards an extended position in which the plunger tip protrudes beyond the housing and the indicator arm is biased towards a first position on the measurement gauge.

The device of the second and third aspects may comprise the device of the first aspect.

BRIEF DESCRIPTION OF THE DRAWINGS

It will be convenient to hereinafter describe the invention in greater detail by reference to the accompanying figures which facilitate understanding of the present invention. Like reference numerals are used to refer to like features. The particularity of the figures and the related description is not to be understood as superseding the generality of the broad identification of the invention as given in the attached claims.

DETAILED DESCRIPTION

Figure 1:
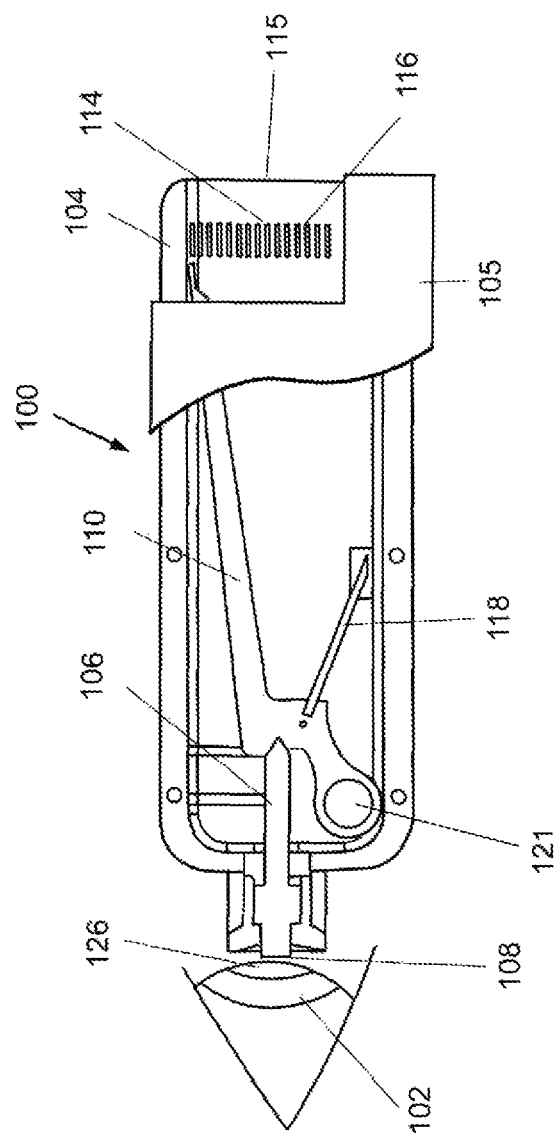
FIG. 1 is a side on view of a device for determining an intraocular pressure of are eye according to one embodiment of the invention during use.

Referring firstly to FIG. 1, there is shown a tonometer or device 100 for determining an intraocular pressure of an eye 102.

The device 100 includes a housing 104, within which the components of the device 100 reside. This arrangement, wherein the components of device 100 are accommodated within housing 104 is of significant advantage because it allows one-handed use and results in a device that is generally easier to use. In addition to allowing one-handed use, device 100 allows use with either a left or a right hand.

One of the components of device 100 comprises a plunger 106 comprising a plunger tip 108, at one end for contacting the eye 102. The other end of the plunger 106 is operably connected to an indicator arm 110.

Figure 2:
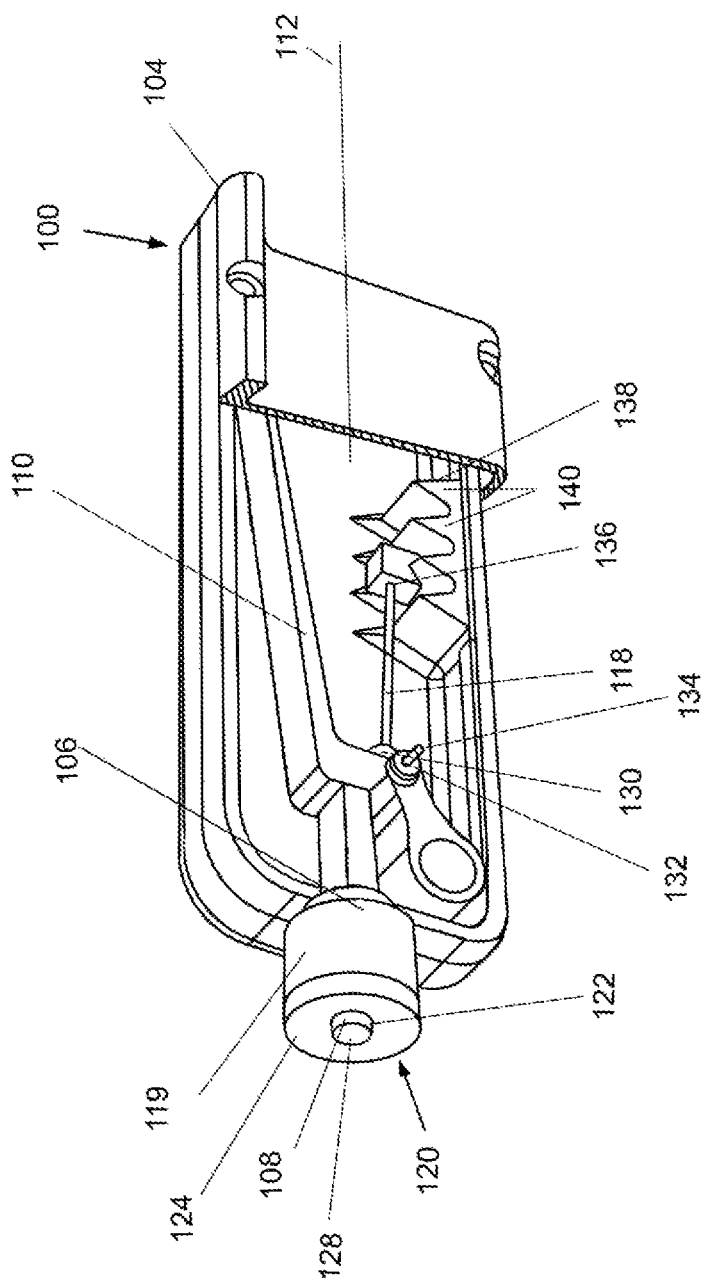
FIG. 2 is a perspective view of the device of FIG. 1.

The plunger 106 is axially movable within the housing 104, that is, the plunger 106 is movable in a direction that is parallel to the longitudinal axis of the housing 112 (see FIG. 2). The extent of axial movement of the plunger 106 allows the plunger tip 108 to extend beyond the extremity of the housing 104 to an extended position and to retract so as to be substantially flush with the extremity of the housing 104.

Due to the operable connection of the plunger 106 to the indicator arm 110, movement of the plunger 106 results in a reciprocal movement in the indicator arm 110. The indicator arm 110 serves to indicate the intraocular pressure of the eye 102 on the measurement gauge 114. Significantly, the embodiment shown in FIG. 1 has indicator arm 110 arranged to pivot in a plane parallel to the longitudinal axis of housing 104. This orientation of indicator arm 110 allows the components of device 100 to be accommodated within housing 104. The measurement gauge 114 comprises a graduated scale 116 to indicate the intraocular pressure. The graduated scale 116 may correspond to various levels of intraocular pressure in mmHg. That is, the graduated scale 116 may be calibrated to provide an actual reading of intraocular pressure in mmHG. Alternatively, the scale 116 may correspond to an approximate indication of LOW, MEDIUM or HIGH intraocular pressure. The graduated scale 116 may be colour coded, whereby a particular colour, say green corresponds to a LOW intraocular pressure, another colour, say yellow corresponds to a MEDIUM intraocular pressure, and yet another colour, say red corresponds to a HIGH intraocular pressure.

For instance, in the case of the colour coded scale the device 100 may be used as a threshold detector of high intraocular pressure, by emergency medical staff or unskilled users to simply determine if the intraocular pressure is normal or high. The calibrated scale providing an actual reading of intraocular pressure in mmHG, on the other hand provides a more sophisticated device permitting intraocular pressure readings to an accuracy of, for example +/−3 mmHg.

The measurement gauge 114 may be adjusted within housing 104 during assembly for pressure reading calibration.

The embodiment shown in FIG. 1, shows housing 104 to comprise a transparent window 115 to allow viewing of measurement gauge 114. Transparent window 115 is located at a distal end of the device, away from where contact is made with eye 102. This positioning of window 115 is accomplished by positioning counterbalance 121 at a proximal end of device 100 so indicator arm 110 points away from the eye.

Operation of the device 100 is effected by means of a resilient biasing member 118. The resilient biasing member 118 biases the plunger 106 towards an extended position wherein the plunger tip 108 protrudes beyond the housing 104. In this extended position, the operably connected indicator arm 110 is biased towards a first position on the measurement gauge 114. This first position could correspond to a null reading, i.e. a zero intraocular pressure, on the measurement gauge 114, or to a predetermined intraocular pressure, for example 10 mmHg. When not in use, the indicator arm 110 is biased towards the first position.

During use, the operator places the device 100 proximate to the eye 102, such that pressure is applied to the eye 102, i.e. the cornea, via the plunger tip 108. The intraocular pressure of the eye 102 will exert an opposing force on the plunger tip 108 which serves to overcome the biasing force provided by the resilient biasing member 118. The plunger 106 is thereby caused to retract, moving axially within the housing 104. This movement of the plunger 104 causes a reciprocal movement of the indicator arm 110 towards a second position in which the indicator arm 110 indicates the intraocular pressure of the subject eye 102 on the measurement gauge 114.

The housing 104, may be encased in a sleeve 105, wherein the housing itself is axially moveable within the sleeve 105 in a direction that is parallel to the longitudinal axis 112 (see FIG. 2) of the housing. The extent of movement of the housing 104 within the sleeve 105 may be calibrated to indicate to an operator of the device 100, when the operator should cease increasing the pressure applied to the eye 102. This level of pressure will correspond to the point where the operator should take a reading from the measurement gauge 114.

Referring now to FIG. 2, the housing 104 of the device 100 includes a tube-like portion 119 at one end through which the plunger tip 108 protrudes when in the extended position. The tube-like portion 119 includes a footplate 120 having an aperture 122, through which the plunger tip 108 extends. This configuration enables the tube-like portion 119 to serve as a guide for axial movement of the plunger 106 within the housing 104.

The footplate 120 has a concave surface 124 that runs substantially perpendicular to the longitudinal axis 112 of the housing 104 and tube-like portion 119. Since the footplate 120 contacts the patient's eye 102, the footplate 120 may be formed of a biocompatible material to avoid damaging the patient's eye 102 and also to make the procedure for determining the intraocular pressure of the eye 102 more comfortable for the patient. Biocompatible materials such as silicon, for example, are less likely to cause discomfort or damage to the cornea. The footplate 120 may also be formed of an elastomeric material having the ability to conform to the surface geometry of the eye 102, thereby making the procedure more comfortable for the patient and less likely to damage to the corneal surface.

The footplate 120 has a diameter which corresponds approximately to the diameter of an iris 126 (see FIG. 1) of the eye 102, this may be in the order of 10 to 15 mm. The contact surface 128 of the plunger tip 108, that is the surface which contacts the eye 102, may be concave to approximate the shape of the cornea. Alternately, the contact surface 128 of the plunger tip 108 may be substantially flat.

In one embodiment, footplate 120 is transparent to allow the operator to easily identify when the footplate 120 makes contact with a cornea of the eye 102.

In FIG. 2, the plunger 106 is shown in the extended position. The plunger 106 is biased towards the extended position by the resilient biasing member 118 as described with reference to FIG. 1. The resilient biasing member 118 may comprise any suitable spring type, but in a particular embodiment of the device of the present invention, the resilient biasing member comprises an elastomeric spring element. The elastomeric spring may be a polymeric spring, for example, formed from acetal, also known as polyacetal, polyoxymethylene (POM), or polyformaldehyde or a polymer such as polyetheretherketone (PEEK). Alternately, the spring could be made from carbon fibre, steel or any other suitable material.

The resilient biasing member 118 has a first end 130 coupled to the indicator arm 110 in the vicinity of a bend 132 in the indicator arm 110. The bend 132 provides a pivot point typically around a pivot pin 134. The pin 134 could be formed from a protruding feature of the indicator arm 110 itself rather than being configured as a discrete element. The indicator arm 110 is preferably counterbalanced about the pivot point such that the device 100 can be used to determine the intraocular pressure of the eye 102 at any angle. That is, the device 100 may be used on a patient who is sitting, or supine, for example.

This is achieved through provision of counterbalance 121, which also pivots around the pivot point, which in the embodiment shown in FIG. 1 comprises pivot pin 134. In the embodiment shown in FIG. 1, indicator arm 110, resilient biasing member 118, and counterbalance 121 are integrated into a single piece. In other embodiments, these components may be assembled from separate components.

The resilient biasing member 118 has a second end 136 which may be fixed in position within the housing 104. Alternately, the position of the second end 136 may be adjustable. Enabling adjustment of the second end of the resilient biasing member 118 relative to the housing 104 permits calibration of the force applied to the indicator arm 110 by the resilient biasing member 118.

In FIG. 2, position of the second end 136 of the resilient biasing member 118 is adjustable along a linear rack 138. The linear rack 138 includes a plurality of teeth 140 to facilitate adjustment of the position of the resilient biasing member 118. In this way, the resilient biasing force can be adjusted to suit the prevailing conditions.

Another means of varying the resilient bias, is to change the length of the resilient biasing member 118. One such means may be a screw knob (not shown) which can be adjusted to lengthen or shorten the resilient biasing member 118. Since the measurement gauge 114, generally has a fixed space from which the intraocular pressure may be read by an operator, adjusting the length of resilient biasing member 118 can effectively extend the extent of the measurement gauge 114. For example, at a particular length, the resilient biasing member 118 may bias the indicator arm 110 to provide a read out in the 10 to 25 mmHg range, while shortening the resilient biasing member 118 may permit a second range of read outs in the 25 to 40 mmHg range. Further adjusting the length, and accordingly the stiffness, of the resilient biasing member 118, could provide further ranges on the measurement gauge 114.

Figure 3:
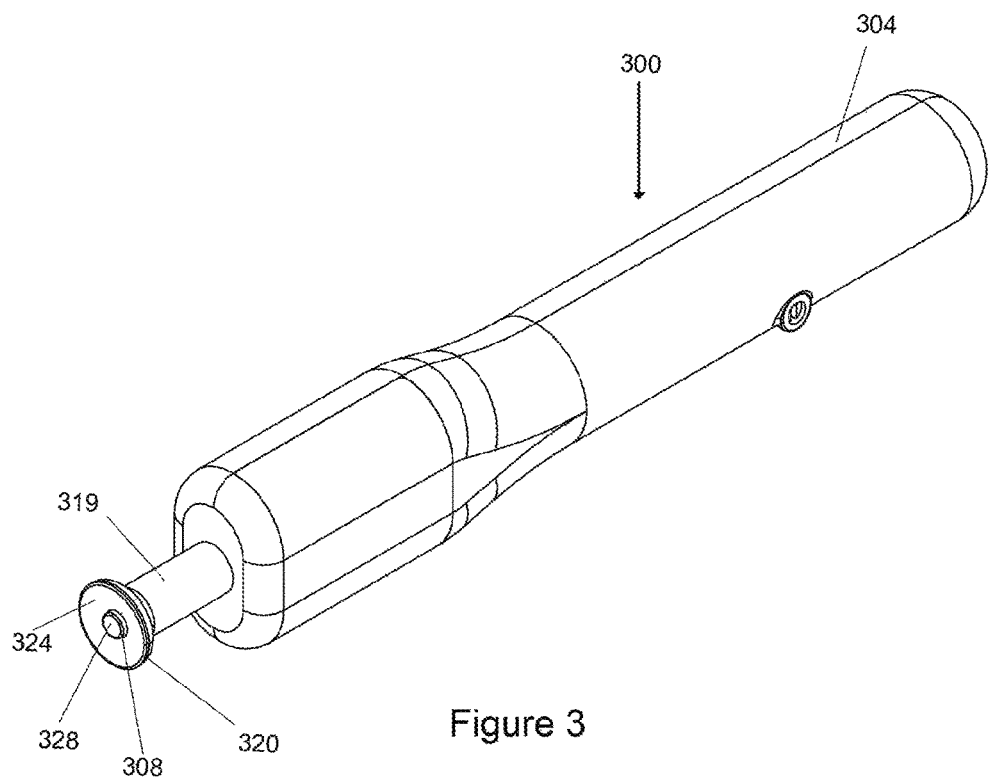
FIG. 3 is a perspective view of an alternate embodiment of a device for determining an intraocular pressure of an eye.
Figure 4:
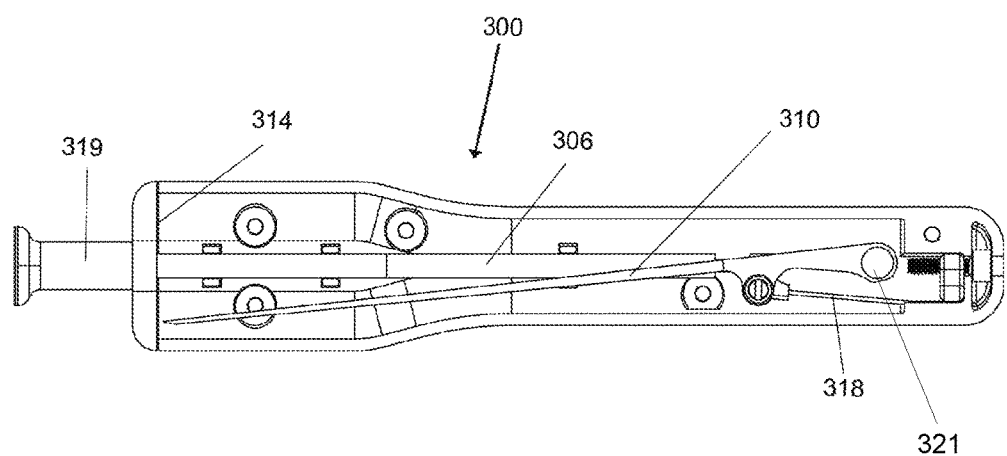
FIG. 4 is a side on view of the device of FIG. 3.

Referring now to FIGS. 3 and 4 there is shown an alternate embodiment of a device 300 for determining an intraocular pressure of an eye 102. FIG. 3 shows the exterior of device 300 including housing 304, the tube-like portion 319 which acts as a guide to the plunger 306 (not shown see FIG. 4). Plunger tip 308 protrudes through the footplate 320 and having a concave surface 324. The footplate 320 and the contact surface 328 of the plunger tip 308 being concave to approximate to the shape of the cornea.

FIG. 4 is a cut away view showing the internal mechanisms of the device 300 which are essentially the same as those described with reference to FIGS. 1 and 2. However, in device 300, the internal mechanism is effectively reversed so that the indicator arm 310 indicates the intraocular pressure of the subject eye 102 on the measurement gauge 114 at the end of the device 100 that is proximal or close to the eye 102. The reversal comprises positioning counterbalance 321 at a distal end of device 300 so that indicator arm 310 points towards the eye 102. This alternate configuration facilitates easy reading of the measurement gauge 314 by the operator of the device 300. The plunger 306 is still operably connected to an indicator arm 310 and biased towards the extended position by resilient biasing member 318.

During use, a high intraocular pressure in the eye 102 will cause a greater retraction of the plunger 106, 306 into the housing 104, 304. That is, a high intraocular pressure causes the cornea to exert a greater opposing force on the plunger tip 108, 308 which overcomes the biasing force provided by the resilient biasing member 118, 318 to cause the plunger 106, 306 to retract into the housing 104, 304. A substantial retraction of the plunger 104, 304 causes a reciprocal movement of corresponding magnitude in the indicator arm 110, 310 to indicate on the measurement gauge 114, 314 that the intraocular pressure is HIGH.

Where the intraocular pressure is approaching a maximum value, the plunger 106, 306 is caused to retract into the housing 104, 304 to the extent that the plunger tip 108, 308 is caused to lie substantially flush with the footplate 120, 320 through which the plunger tip 108, 308 protrudes.

On the other hand, a low intraocular pressure in the eye 102, 302 causes a lesser retraction of the plunger 106, 306. That is, the intraocular pressure exerts a lesser opposing force on the plunger tip 108, 308 which overcomes the biasing force provided by the resilient biasing member 118, 318 to cause the plunger 106, 306 to retract into the housing 104, 305. A small retraction of the plunger 106, 306 causes a reciprocal movement of corresponding lesser magnitude in the indicator arm 110, 310 to indicate on the measurement gauge 114, 314 that the intraocular pressure is LOW.

Figure 5:
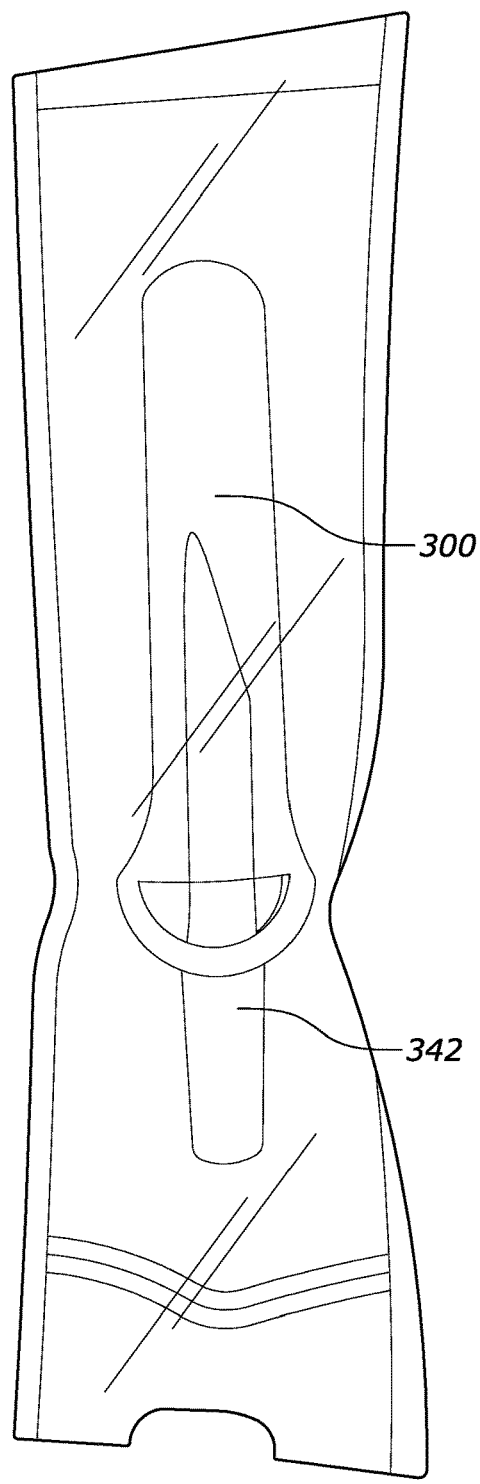
FIG. 5 is a photograph of another embodiment of a device according to the invention packaged and ready for use.

FIG. 5 shows an embodiment of the device 300 according to the alternate embodiment of FIGS. 3 and 4 packaged and ready for use. The packaged device comprises a protective cap 342. Protective cap 342 extends over plunger tip 308 to protect from damage during shipping and storage. Once ready for use, the protective cap 342 can be pulled off to remove it and permit application of tip 308 to eye 102.

A method for determining an intraocular pressure of an eye is also provided using the device as described with reference to FIGS. 1 to 5. Due to the lightweight and compact configuration of the device 100, 300 it is configured such that the device 100 may be operated by a single hand.

Furthermore lightweight and compact configuration of the device 100, 300 makes the tonometer 100, 300 of the present invention cost effective to manufacture, enabling the device 100, 300 to be offered as a single use device. The disposable nature of the device 100, 300 is advantageous in that it can be provided in a sterile form for hygienic use in a clinic environment.

It is an advantage of the device 100, 300 of the present invention, is that it is simple to operate even by operators that have received minimal training as well as being minimally invasive. The device 100, 300 can be used at any angle, that is, with the patient sitting, or supine. Moreover, the device 100, 300 may be used in either a left hand or a right hand.

The device is inexpensive to manufacture and provides a range of intraocular pressure measurements ranging from around 10 mmHg to 50 mmHg.

While the invention has been, described in conjunction with a limited number of embodiments, it will be appreciated by those skilled in the art that many alternative, modifications and variations in light of the foregoing description are possible. Accordingly, the present invention is intended to embrace all such alternative, modifications and variations as may fall within the spirit and scope of the invention as disclosed.

The present application may be used as a basis or priority in respect of one or more future applications and the claims of any such future application may be directed to any one feature or combination of features that are described in the present application. Any such future application may include one or more of the following claims, which are given by way of example and are non-limiting in regard to what may be claimed in any future application.

The invention claimed is:

1. A device for determining an intraocular pressure of an eye of a patient comprising:
   (a) a housing;
   (b) a plunger axially movable within the housing, a first end of the plunger having a tip for contacting the eye;
   (c) an indicator arm operatively connected to a second end of the plunger;
   (d) a measurement gauge for indicating the intraocular pressure of the eye;
   (e) a resilient biasing member having a first end coupled to the indicator arm for biasing the plunger towards an extended position in which the plunger tip protrudes beyond the housing and the indicator arm is biased towards a first position on the measurement gauge; and
   (f) a counterbalance for balancing the indicator arm about a pivot such that the device can be used to determine the intraocular pressure of the eye when the plunger is contacting the eye from multiple angles;
   wherein applying pressure to the eye via the plunger tip causes the intraocular pressure of the eye to exert an opposing force on the plunger tip causing the plunger to retract into the housing to cause a reciprocal movement of the indicator arm towards a second position thereby indicating the intraocular pressure of the eye on the measurement gauge; and
   wherein the gauge and indicator arm are comprised within the housing;
   wherein the indicator arm pivots in a plane parallel to the longitudinal axis of housing when pressure is applied to the eye via the plunger tip and the indicator is moving from the first position towards the second position; and
   wherein the indicator arm, resilient biasing member, and counterbalance are integrated into a single piece.

2. A method for determining an intraocular pressure of an eye of a patient including the step of applying pressure to the eye of the patient using a device, the device including:
   (a) a housing;
   (b) a plunger axially movable within the housing, a first end of the plunger having a tip for contacting the eye;
   (c) an indicator arm operatively connected to a second end of the plunger;
   (d) a measurement gauge for indicating the intraocular pressure of the eye;
   (e) a resilient biasing member having a first end coupled to the indicator arm for biasing the plunger towards an extended position in which the plunger tip protrudes beyond the housing and the indicator arm is biased towards a first position on the measurement gauge; and
   (f) a counterbalance for balancing the indicator arm about a pivot such that the device can be used to determine the intraocular pressure of the eye when the plunger is contacting the eye from multiple at any angles;
   wherein applying pressure to the eye via the plunger tip causes the intraocular pressure of the eye to exert an opposing force on the plunger tip causing the plunger to retract into the housing to cause a reciprocal movement of the indicator arm towards a second position thereby indicating the intraocular pressure of the eye on the measurement gauge;
   wherein the gauge and indicator arm are comprised within the housing;
   wherein the indicator arm pivots in a plane parallel to the longitudinal axis of housing when pressure is applied to the eye via the plunger tip and the indicator is moving from the first position towards the second position; and
   wherein the indicator arm, resilient biasing member, and counterbalance are integrated into a single piece.

3. A method for manufacturing a device for determining an intraocular pressure of an eye comprising:
   assembling within a housing an axially moveable plunger, a first end of the plunger comprising a tip for contacting the eye, an indicator arm operatively connected to a second end of the plunger, a measurement gauge for indicating the intraocular pressure of the eye, and a resilient biasing member having a first end coupled to the indicator arm for biasing the plunger towards an extended position in which the plunger tip protrudes beyond the housing and the indicator arm is biased towards a first position on the measurement gauge, and a counterbalance for balancing the indicator arm about a pivot such that the device can be used to determine the intraocular pressure of the eye when the plunger is contacting the eye from multiple angles;
   wherein the gauge and indicator arm are comprised within the housing;
   wherein the indicator arm pivots in a plane parallel to the longitudinal axis of housing when pressure is applied to the eye via the plunger tip and the indicator is moving from the first position towards the second position; and
   wherein the indicator arm, resilient biasing member, and counterbalance are integrated into a single piece.

4. The device of claim 1, wherein the measurement gauge is adjusted within the housing during assembly for pressure reading calibration.

5. The device of claim 1, wherein the housing comprises a transparent window to allow viewing of the measurement gauge.

6. The method of claim 2, wherein the measurement gauge is adjusted within the housing during assembly for pressure reading calibration.

7. The method of claim 2, wherein the housing comprises a transparent window to allow viewing of the measurement gauge.

8. The method of claim 3, wherein the measurement gauge may be adjusted within the housing during assembly for pressure reading calibration.

9. The device of claim 1, wherein the housing includes a tube-like portion at one end through which the plunger tip protrudes in the extended position.

10. The device of claim 9, wherein the tube-like portion comprises a footplate having an aperture through which the plunger tip protrudes.

11. The device of claim 10, wherein the footplate comprises a concave surface that runs substantially perpendicular to a longitudinal axis of the tube-like portion.

12. The device of claim 10, wherein the footplate is transparent to allow an operator to easily identify when the footplate makes contact with a cornea of the eye.

13. The method of claim 2, wherein the housing includes a tube-like portion at one end through which the plunger tip protrudes in the extended position.

14. The method of claim 13, wherein the tube-like portion comprises a footplate having an aperture through which the plunger tip protrudes.

15. The method of claim 14, wherein the footplate comprises a concave surface that runs substantially perpendicular to a longitudinal axis of the tube-like portion.

16. The method of claim 14, wherein the footplate is transparent to allow an operator to easily identify when the footplate makes contact with a cornea of the eye.

17. The method of claim 3, wherein the housing includes a tube-like portion at one end through which the plunger tip protrudes in the extended position.

18. The method of claim 17, wherein the tube-like portion comprises a footplate having an aperture through which the plunger tip protrudes.

19. The method of claim 18, wherein the footplate comprises a concave surface that runs substantially perpendicular to a longitudinal axis of the tube-like portion.

20. The method of claim 18, wherein the footplate is transparent to allow an operator to easily identify when the footplate makes contact with a cornea of the eye.

* * * * *